United States Patent
Claus et al.

(10) Patent No.: US 9,532,757 B2
(45) Date of Patent: Jan. 3, 2017

(54) C-ARM SYSTEM AND C-ARM SPIN ACQUISITION TRAJECTORIES FOR DYNAMIC IMAGING AND IMPROVED IMAGE QUALITY AND METHOD OF USE

(71) Applicant: General Electric Company, Schenectady, NY (US)

(72) Inventors: Bernhard Erich Hermann Claus, Niskayuna, NY (US); David Allen Langan, Clifton Park, NY (US); Omar Al Assad, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 199 days.

(21) Appl. No.: 14/319,309

(22) Filed: Jun. 30, 2014

(65) Prior Publication Data
US 2015/0374319 A1  Dec. 31, 2015

(51) Int. Cl.
*A61B 6/00* (2006.01)
*A61B 6/02* (2006.01)
*A61B 6/03* (2006.01)

(52) U.S. Cl.
CPC ............. *A61B 6/4441* (2013.01); *A61B 6/027* (2013.01); *A61B 6/032* (2013.01); *A61B 6/486* (2013.01); *A61B 6/507* (2013.01)

(58) Field of Classification Search
CPC ..... A61B 6/027; A61B 6/4405; A61B 6/4441; A61B 6/4447; A61B 6/035; A61B 6/4476
See application file for complete search history.

(56) References Cited

U.S. PATENT DOCUMENTS

| | | |
|---|---|---|
| 2003/0013953 A1 | 1/2003 | Mistretta |
| 2005/0135558 A1 | 6/2005 | Claus et al. |
| 2005/0243962 A1 | 11/2005 | Grass et al. |
| 2006/0023830 A1* | 2/2006 | Schomberg ............ A61B 6/032 378/4 |
| 2008/0037700 A1 | 2/2008 | Grass et al. |
| 2008/0118023 A1 | 5/2008 | Besson |
| 2012/0121062 A1 | 5/2012 | Sowards-Emmerd et al. |
| 2012/0189094 A1 | 7/2012 | Neushul et al. |
| 2013/0303884 A1 | 11/2013 | Kuntz et al. |

OTHER PUBLICATIONS

Strobel et al. "Imaging with Flat-Detector C-Arm Systems", Multislice CT Medical Radiology, pp. 33-51, 2009.

* cited by examiner

*Primary Examiner* — Hoon Song
(74) *Attorney, Agent, or Firm* — Melissa K. Dobson

(57) ABSTRACT

C-arm systems and method for making and using continuous C-arm spin acquisition trajectories for dynamic imaging and improved image quality are described. In such systems and methods, a C-arm gantry, coupled to a C-arm support assembly, is adapted to retain an x-ray source and an x-ray detector. The C-arm gantry is selectively rotatable relative to the C-arm support assembly about both a C-arm axis and a pivot-axis to displace the x-ray source and the x-ray detector along a continuous C-arm spin trajectory. The C-arm system is adapted for continuous three-dimensional acquisition of data along the continuous C-arm spin trajectory including a plurality of shorts arcs and a plurality of long arcs. The C-arm system is adapted for continuous three-dimensional acquisition of data along the continuous C-arm spin trajectory to provide continuous three-dimensional imaging of dynamic processes.

20 Claims, 7 Drawing Sheets

C-ARM SYSTEM AND C-ARM SPIN ACQUISITION TRAJECTORIES FOR DYNAMIC IMAGING AND IMPROVED IMAGE QUALITY AND METHOD OF USE

BACKGROUND

The disclosure relates generally to X-ray equipment. More specifically, this application relates to C-arm spin acquisition trajectories of an X-ray machine, and more particularly to C-arm spin acquisition trajectories that enable 3D imaging of dynamic processes.

X-ray machines are known devices that allow individuals, such as healthcare practitioners, to capture images, in a relatively non-intrusive manner, of bones and other tissues, bone density, implanted devices, catheters, pins, and a wide variety of other objects and materials that are within a patient's body. In this regard, the term X-ray may refer to any suitable type of X-ray imaging, including film X-ray shadow grams and X-ray fluoroscopic imaging, which may refer to images that are produced by the conversion of an incident X-ray pattern to a "live" enhanced or intensified optical image that can be displayed on a video monitor, nearly contemporaneously with the irradiation of the portion of the patient's body that is being imaged.

Often, when a practitioner takes X-rays of a patient, it is desirable to take several X-rays of one or more portions of the patient's body from a number of different positions and angles, and preferably without needing to frequently reposition the patient. To meet this need, C-arm X-ray diagnostic equipment has been developed. The term C-arm generally refers to an X-ray imaging device having a rigid and/or articulating structural member having an X-ray source and an image detector assembly that are each located at an opposing end of the structural member so that the X-ray source and the image detector face each other. The structural member is typically "C" shaped and so is referred to as a C-arm. In this manner, X-rays emitted from the X-ray source can impinge on the image detector and provide an X-ray image of the object or objects that are placed between the X-ray source and the image detector.

In many cases, C-arms are connected to a movable support. In such cases, the C-arm can often be raised and lowered, be moved from side to side, and/or be rotated about one or more axes of rotation. Accordingly, such C-arms can be moved and reoriented to allow X-ray images to be taken from several different positions and angles and different portions of a patient, without requiring the patient to be repositioned.

When images are acquired from a number of different gantry angles (i.e., for different orientations of the C-arm with respect to the imaged region of interest), these images may be reconstructed into a volumetric representation of the structures of the object contained in the imaged region. Generally, such an acquisition is performed by using a so-called spin acquisition, i.e., by rotating the C-arm gantry by about 200-220 degrees around a rotational axis. This limitation of the angular range is a consequence of mechanical limitations of the gantry, which, in particular, does not allow for a continuous rotation along a single axis of rotation. However, this angular range also corresponds to the angular range required for (nearly) complete data (e.g., 180 degrees plus the fan angle), and high-quality 3D images may be reconstructed from the collected data. In situations where a sequence of 3D datasets is to be acquired, the spin acquisition may be repeated periodically (and the gantry moved back to the start position in-between spins), or a back-and-forth spin acquisition may be performed, where x-ray image data is acquired during both directions of motion of the gantry.

Current approaches for use of these C-arm devices consist of a sequence of back-and-forth spin acquisitions. Of particular interest is the use of this back-and forth spin using a C-arm in order to acquire data for dynamic 3D imaging, such as perfusion imaging. Specifically, the dynamic nature of the perfusion is accommodated by acquiring a number of consecutive spin datasets, where the delay between consecutive datasets is minimized by acquiring data both on the forward spin, and on the backward spin. However, a significant drawback of this method consists of the fact that there is still a dead-time of about 1.5 seconds between the end of the spin acquisition in one direction, and the start of the acquisition in the other direction. This delay is due mainly to mechanical reasons (allow gantry vibrations to settle). No data is collected during this dead-time, which is mostly due to the fact that the data is from a single, static gantry position, and thereby does not provide any 3D information.

Accordingly, a means for acquiring data along a trajectory whereby this dead-time is eliminated, thereby minimizing gantry vibration and enabling improved image quality as a result of increased data completeness, is desirable.

BRIEF DESCRIPTION

These and other shortcomings of the prior art are addressed by the present disclosure, which provides an apparatus includes C-arm system and c-arm spin acquisition trajectories for dynamic imaging and improved image quality.

One aspect of the present disclosure resides in a C-arm system including a C-arm support assembly and a C-arm gantry coupled to the C-arm support assembly. The C-arm gantry is adapted to retain an x-ray source and an x-ray detector. The C-arm gantry is selectively rotatable relative to the C-arm support assembly about both a C-axis and a pivot-axis to displace the x-ray source and the x-ray detector along a continuous C-arm spin trajectory. The C-arm system is adapted for continuous three-dimensional acquisition of data along the continuous C-arm spin trajectory comprised of a plurality of shorts arcs and a plurality of long arcs to provide continuous three-dimensional imaging of dynamic processes.

In accordance with another exemplary embodiment of the present disclosure, another aspect of the present disclosure resides in a C-arm system including a C-arm support assembly and a C-arm gantry coupled to the C-arm support assembly. The C-arm gantry is adapted to retain an x-ray source and an x-ray detector. The C-arm gantry is selectively rotatable relative to the C-arm support assembly about both a C-arm axis and a pivot-axis to displace the x-ray source and the x-ray detector along a continuous C-arm spin trajectory. The continuous C-arm spin trajectory comprises a plurality of short arcs and a plurality of long arcs and wherein a motion along a substantial part of each of a plurality of long arcs of the continuous C-arm spin trajectory utilizes only the pivot-axis, with the C-arm rotational axis in a fixed position. The C-arm system is adapted for continuous three-dimensional acquisition of data along the continuous C-arm spin trajectory to provide continuous three-dimensional imaging of dynamic processes.

In accordance with another exemplary embodiment of the present disclosure, a method for using a C-arm system includes providing a C-arm support assembly and a C-arm gantry coupled to the C-arm support assembly, controlling one or more motors operatively connected to the C-arm gantry to induce a selectable amount of C-arm gantry rotation relative to an imaged object along a continuous C-arm spin trajectory and continuously acquiring data along the continuous C-arm spin trajectory to provide continuous three-dimensional imaging of dynamic processes. The C-arm gantry is adapted to retain an x-ray source and an x-ray detector;

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Embodiments of the present disclosure relate to generalized C-arm spin acquisition trajectories using a C-arm x-ray device for dynamic 3D imaging and improved image quality. The following description supplies specific details in order to provide a thorough understanding. Nevertheless, the skilled artisan will understand that the described C-arm devices and associated methods of using the devices can be implemented and used without employing these specific details. Indeed, the C-arm devices and associated methods can be placed into practice by modifying the described devices and methods and can be used in conjunction with any other apparatus and techniques conventionally used in the industry. For example, while the description below focuses on methods for using standard C-arms, the methods can also be used with mini C-arm devices. As used herein, trajectories are applicable to various types of C-arm x-ray applications such as, but not limited to, 3D imaging of dynamic processes, e.g., imaging for perfusion, imaging for tracking of the progress of an interventional procedure, tracking of tools, etc., 3D imaging where an improved degree of data completeness is desired, etc. In addition, as used herein, singular forms such as "a", "an", and "the" include plural referents unless the context clearly dictates otherwise.

As discussed in detail below, embodiments of the disclosure include a C-arm system configured to have a 2-axis trajectory, describing in its conceptually simplest form a "rectangle" (inscribed on the surface of a sphere), where the long sides of the rectangle consist of offset versions of the (centered) simple spin trajectory (approximately 200-220 degrees), and the end-points of these long arcs are joined by shorter arcs (approximately 15-19 degrees). More specifically, in the context of this disclosure, a trajectory inscribed within a rectangle and comprised of a plurality of short arcs and long arcs is referred to as a continuous C-arm spin trajectory.

Figure 1:
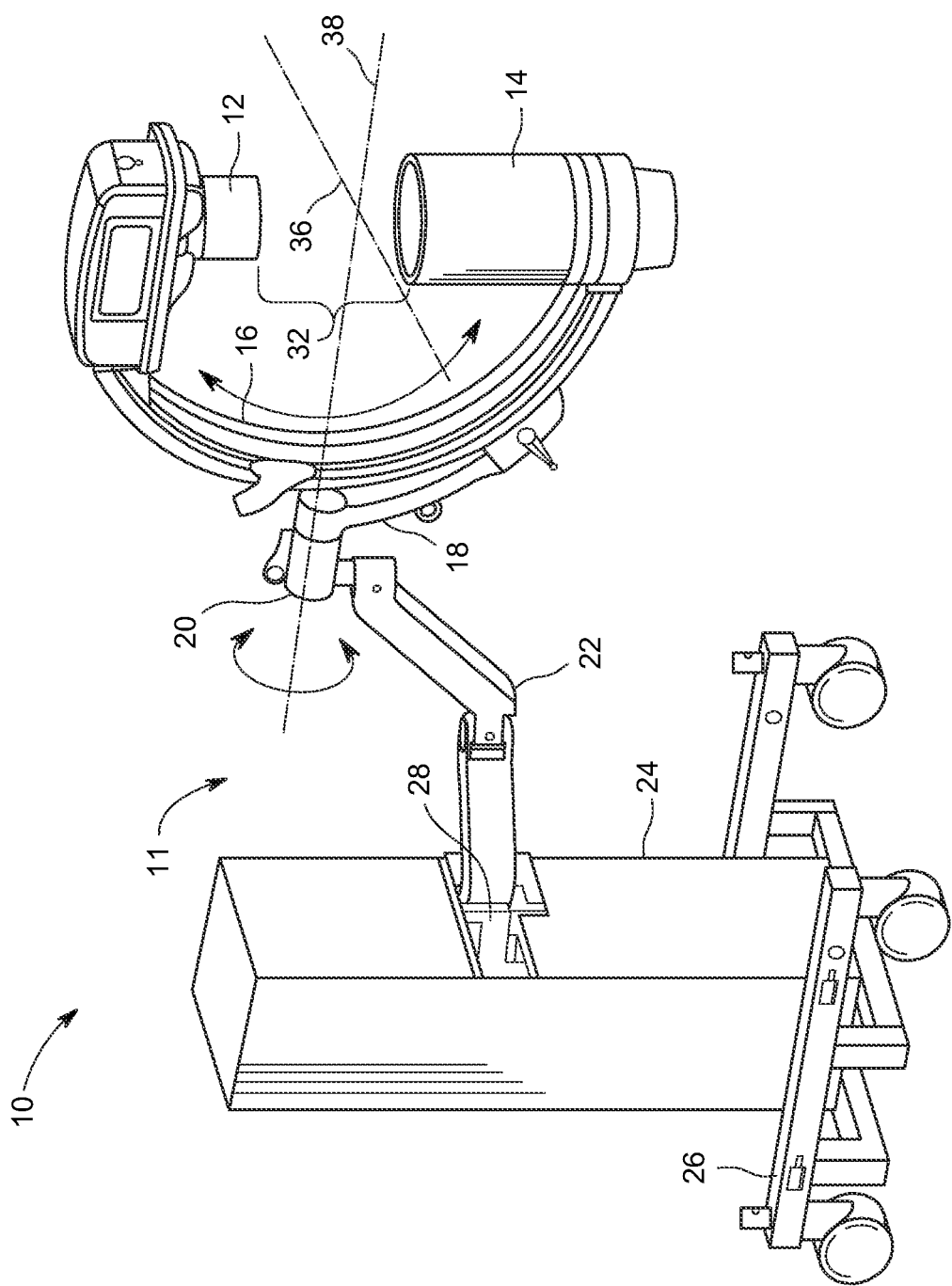
FIG. 1 is a front perspective view of an embodiment of a C-arm system according to one or more embodiments disclosed herein.

Referring now to FIG. 1, a C-arm system 10 is shown in the home position in accordance with an embodiment. The term "C-arm" generally refers to the shape of a conventional C-arm gantry (sometimes referred to as the C-gantry), however, it should be appreciated that, for purposes of this disclosure, terms such as C-arm, C-gantry and C-extension may encompass other shapes and orientations. The "home position" is that shown in FIG. 1 wherein an x-ray source 12 is at the top most or twelve o'clock position and the x-ray detector 14 is at the bottom most or six o'clock position. In an alternate embodiment, such as that illustrated in FIG. 2, the "home position" is wherein the x-ray detector 14 is at the top most or twelve o'clock position and the x-ray source 12 is at the bottom most or six o'clock position.

Referring again to FIG. 1, the C-arm system 10 includes a C-arm support assembly 11 coupled to a C-arm gantry or C-gantry 16. The C-arm support assembly 11 is generally comprised of a C-arm extension or C-extension 18, a C-arm rotational support 20, a C-arm support arm 22 and a C-arm support structure 24, including a bearing rail support structure 26, and/or a C-arm rotational system 28. To provide a better understanding of the C-arm positioning device, each of the aforementioned components is described below in more detail.

The C-arm rotational support 20 rotatably supports the C-extension 18 and/or the C-gantry 16 while remaining stationary relative thereto. In the context of our discussion we refer to a rotation around this axis as a rotation around the pivot axis, which is a rotation around axis 38. The C-gantry 16 and the C-extension 18 are independently rotatable. We refer to a rotation around this axis as a rotation around the C-axis (or C-arm axis), which is a rotation around axis 36. In the embodiment shown in FIG. 1, the orientation of the C-arm rotation axis 36 depends on the angular position of the pivot axis 38. The x-ray source 12 and the x-ray detector 14 are generally rigidly attached to opposing end portions of the C-gantry 16 such that these components are collectively rotatable as a single unit. The x-ray source 12 emits x-rays (not shown) that are detectable by the x-ray detector 14. The x-ray source 12 and the x-ray detector 14 are configured such that when an object is interposed therebetween and is irradiated with x-rays, the x-ray detector 14 produces data representative of characteristics of the interposed object. This representative data can be processed in a known manner to generate an image of the interposed object.

Figure 2:
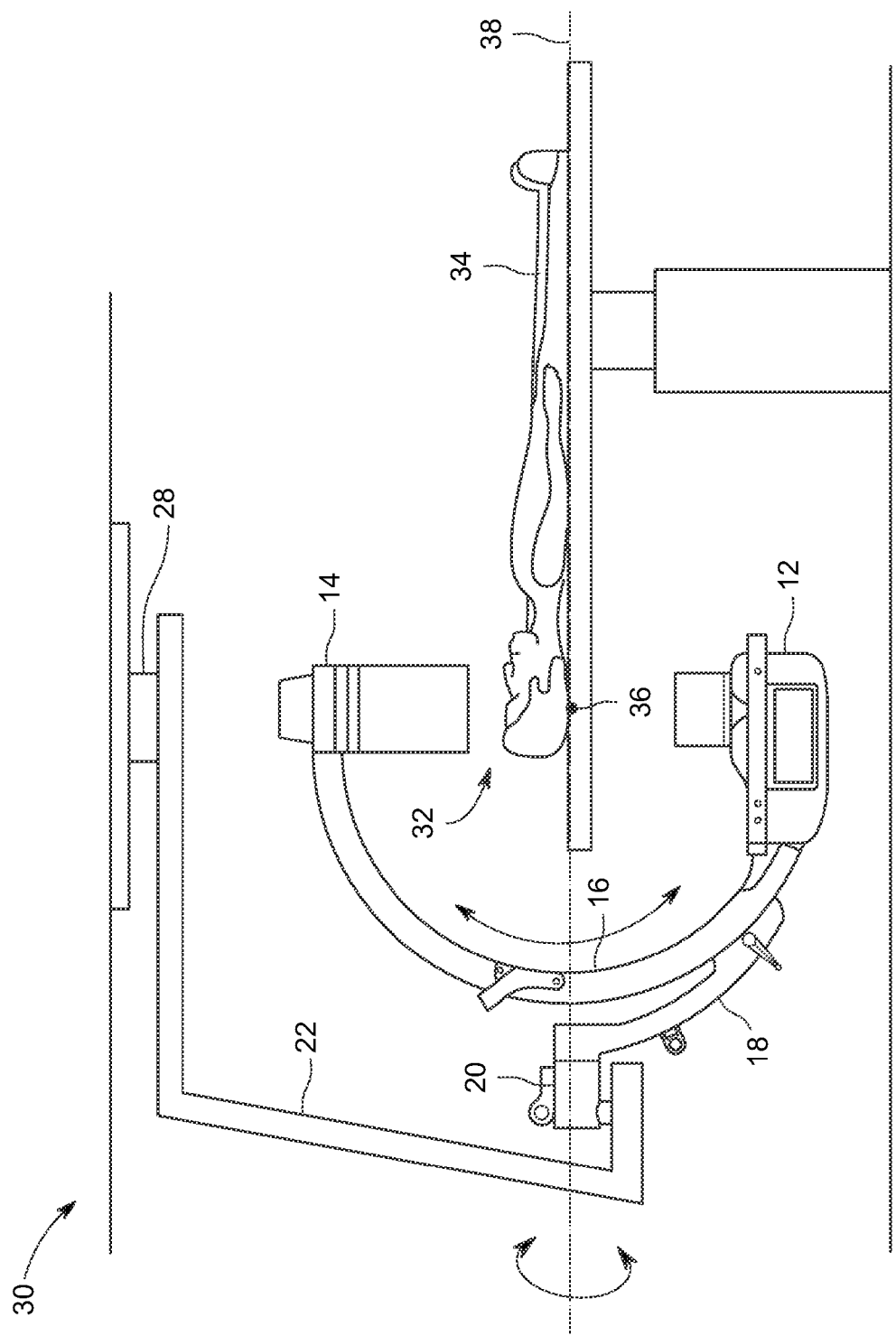
FIG. 2 is a side view of an alternate embodiment of a C-arm system according to one or more embodiments disclosed herein.

The C-gantry 16 can comprise any suitable C-arm that allows the C-arm system 10 to be used to take X-ray images of a portion of a patient's body (not shown). For example, the C-arm can comprise a mini C-arm, a standard C-arm, a fixed x-ray detector and source structure, a variable x-ray detector and source structure and/or any other suitable type of C-arm X-ray assembly. By way of illustration, FIG. 1 shows an embodiment in which the C-arm system 10 is configured as a mobile C-arm system. In an alternate embodiment, as best illustrated in FIG. 2, in which like elements have like numbers as those previously described with reference to FIG. 1, a C-arm system 30 is illustrated and configured as a ceiling mounted C-arm system.

The C-arm system 10, 30 can also comprise any suitable component that allows it to function as intended. For example, FIGS. 1 and 2 illustrate embodiments in which the C-arm system 10, 30 comprises the X-ray source 12 and the X-ray image detector 14 that are respectively disposed at nearly opposite ends of the C-arm gantry 16 so as to face each other. The X-ray image detector 14 can be any known detector, including a digital flat panel detector or an image intensifier. FIGS. 1 and 2 also show that the X-ray source 12 and image detector 14 are spaced apart to define a gap 32 that is large enough to allow a portion of a patient's body 34 (FIG. 2) (e.g., thorax, head, an extremity, etc.) to be inserted into the path of the X-ray beam (not shown) for X-ray imaging. The C-arm C-gantry 16 is configured so as to be rotatable about a C-axis 36 and a pivot-axis 38. The C-axis 36 is typically a "slow" motion axis and corresponds to a short arc of a trajectory, as described presently. The pivot-axis 38 is typically a "fast" motion axis, and corresponds to a long arc of a trajectory and is the axis used for spin acquisitions, as described presently. The combined motion of the C-axis 36 and the pivot-axis 38 allows for the X-ray source 12 to be positioned (within certain limits given by the range of motion of the C-arm gantry 16) at any given point on the surface of a conceptual sphere (as described presently), where the center of the sphere is the center of the field of view (defined approximately by the point where the axes of rotation 36, 38 of the system intersect). The C-arm system 10, 30 is configured to laterally access a stationary object, such as the patient 34 (FIG. 2), either from the side, or from the head (or any angle in-between). More precisely, the gap 32 accommodates the stationary object as the C-arm system 10, 30 (and/or the table supporting the imaged object or patient) is translated into position such that intersection of the C-axis 36 and the pivot-axis 38 generally coincide with the object's region of interest (e.g., a human extremity). Thereafter, the x-ray source 12 and the x-ray detector 14 are rotatable around the C-axis 36 and/or the pivot-axis 38 to obtain a comprehensive three-dimensional image of the region of interest. It is noted that in the context of this disclosure, gantry trajectories and/or view angles, may be described with respect to a sphere as described herein.

For illustrative purposes, this disclosure will hereinafter be described in accordance with an embodiment wherein the C-extension 18 rotation (also referred to as the pivot axis) and the C-gantry 16 rotation (C-arm rotational axis, or C-axis) are induced by one or more motors (not shown) operatively connected thereto. It should be appreciated, that C-gantry 16 and C-extension 18 rotation may be induced in any known manner such as, for example, by a single motor operatively connected to both components, by dual motors, each operatively connected to one of the C-extension 18 or the C-gantry 16, or by other types of power sources. A controller (not shown) is operatively connected to the motor(s) and adapted to operate the motor(s) and thereby selectively rotate the C-gantry 16 and/or the C-extension 18 as will be described in detail hereinafter.

Figure 3:
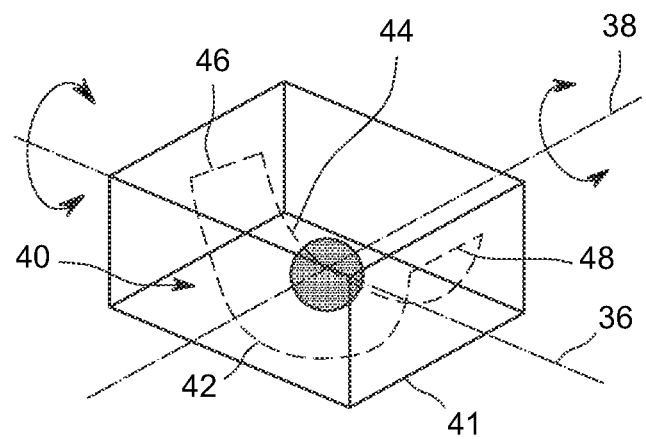
FIG. 3 is a perspective view of a continuous C-arm spin trajectory of a C-arm system according to one or more embodiments disclosed herein.
Figure 4:
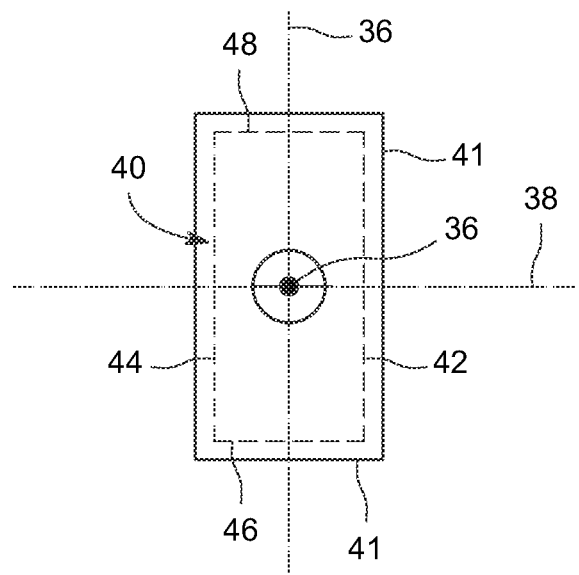
FIG. 4 is a top plan view of the continuous C-arm spin trajectory of FIG. 3 according to one or more embodiments disclosed herein.

Trajectories of known C-arm systems for the acquisition of 3D datasets typically are configured as a single-axis trajectory, and particularly as an arc of a circle which extends through an isocenter of the C-arm system in the transverse plane and where each spin covers an angle of approximately 200-220 degrees. Trajectories of this kind are accomplished by rotating the C-arm about one of the pivot-axis or about the C-arm axis of the C-arm system. Such a trajectory is represented by a line inscribed on the surface of the sphere. Referring now to FIGS. 3 and 4, as previously indicated, the present disclosure provides a C-arm system 10, 30 that is configured having a 2-axis trajectory for the acquisition of 3D datasets. More specifically, the two-axis trajectory, describes in its conceptually simplest form, a "rectangle" (inscribed on the surface of a sphere), where the long sides of the rectangle consist of offset versions of the (centered) single spin trajectory, covering approximately 200-220 degrees, and the end-points of these long arcs are joined by shorter arcs, covering approximately 15-19 degrees. Referring again to FIGS. 1 and 2, during the C-arm gantry 16 motion, the x-ray source 12 follows a trajectory following the circumference of the rectangle (as illustrated in FIGS. 3 and 4). Acquiring x-ray data while following this trajectory periodically and repeatedly enables, e.g., the acquisition of 3D datasets representative of a dynamically evolving process.

Figure 5:
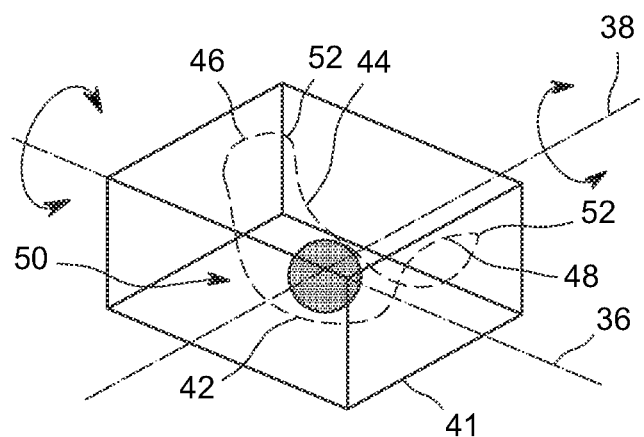
FIG. 5 is a perspective view of a continuous C-arm spin trajectory of a C-arm system according to one or more embodiments disclosed herein.
Figure 6:
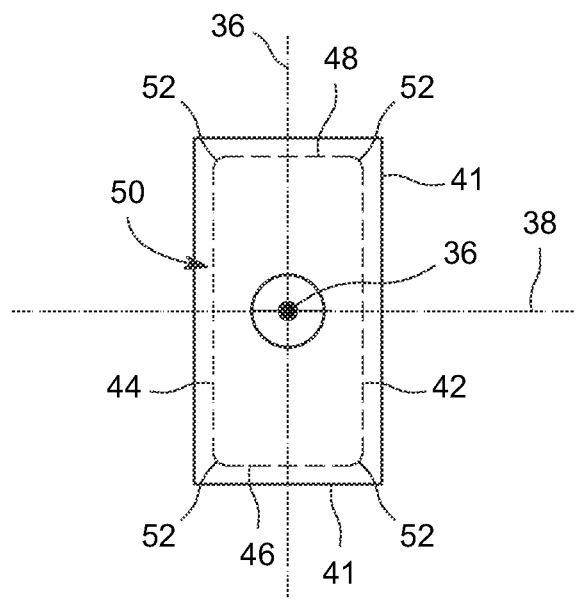
FIG. 6 is a top plan view of the continuous C-arm spin trajectory of FIG. 5 according to one or more embodiments disclosed herein.

As previously indicated, the dynamic nature of the imaged process (e.g., perfusion) is accommodated by continuously acquiring data without dead-time, while the gantry is moving along such a trajectory that may additionally be designed to exhibit minimized gantry vibration, in particular at the turning points. To acquire such continuous data, as best illustrated in FIGS. 3 and 4, an exemplary trajectory 40, inscribed within a bounding rectangle 41, according to an embodiment, includes a first long arc 42, corresponding to a forward spin and a second long arc 44 corresponding to a backward spin. The trajectory 40 further includes a first short arc 46, corresponding to a forward (partial) rotation of the gantry around the C-axis and a second short arc 48, corresponding to a backward (partial) rotation of the gantry around the C-axis. In one embodiment, the motion along each of the long arcs 42, 44 utilizes only the pivot-axis 38, or the propeller axis (with the C-axis 36 in a fixed position), and the motion along the short arcs 46, 48 utilizes only the C-axis 36 (with the pivot-axis 38 in a fixed position). Continuously acquiring x-ray data while continuously and repeatedly traversing the trajectory 40 enables continuous 3D imaging of dynamic processes (e.g., perfusion), and offers improved image quality (through improved data completeness), as well as other advantages. In this and other embodiments, various considerations with respect to gantry speed, gantry vibration, data completeness and angular sampling are taken into account. In an embodiment, a sampling/x-ray view acquisition rate is adjusted to an instantaneous angular speed of the C-gantry 25 (i.e., approximately constant angular spacing between acquired X-ray views). In an alternate embodiment, as best illustrated in FIGS. 5 and 6, the "rectangular" gantry trajectory may be approximated by a trajectory 50 where the corners of the "rectangle" are replaced by a smooth transition 52, for improved mechanical stability and implementation.

Figure 7:
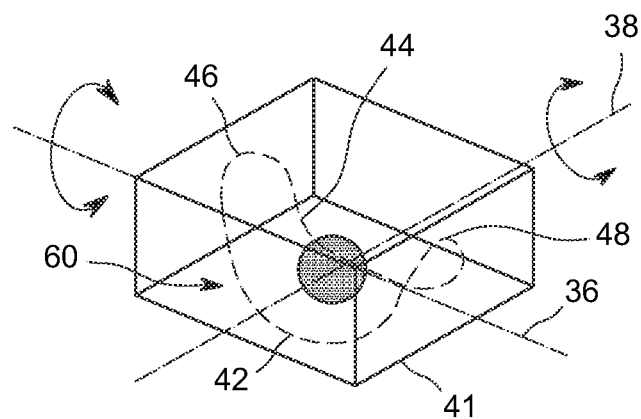
FIG. 7 is a perspective view of a continuous C-arm spin trajectory of a C-arm system according to one or more embodiments disclosed herein.
Figure 8:
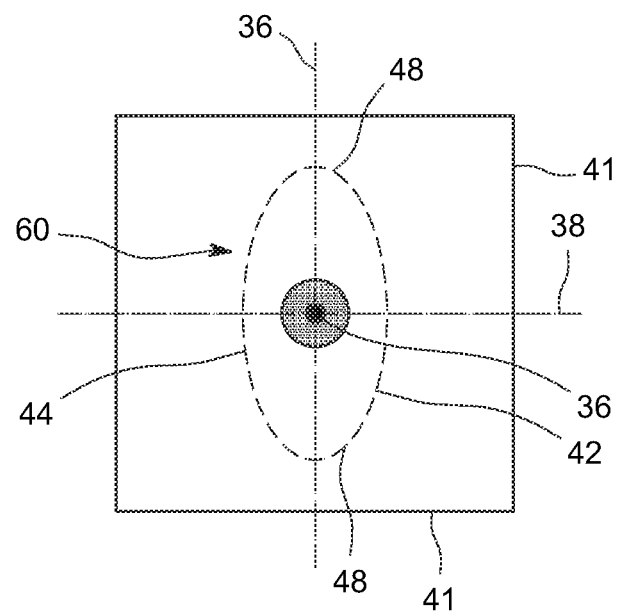
FIG. 8 is a top plan view of the continuous C-arm spin trajectory of FIG. 7 according to one or more embodiments disclosed herein.

In one embodiment, the trajectory along the long arcs utilizes substantially one motion axis, while the trajectory along the short arcs utilizes another motion axis, and in the smooth transition regions between arcs both motion axes are utilized simultaneously. For example, the trajectory along each of the long arcs may utilize substantially the pivot axis, while the C-axis remains in a fixed position. The trajectory along each of the short arcs may use the C-axis, while the pivot axis remains in a fixed position. In the transition regions, both axes may be utilized. In yet another embodiment, a substantially elliptical trajectory 60, as best illustrated in FIGS. 7 and 8, may be used.

Figure 9:
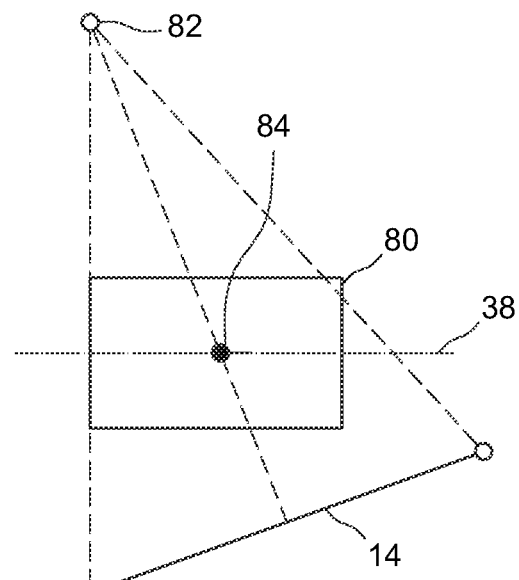
FIG. 9 is a side view of the cylindrical (nominal) field-of-view according to one or more embodiments disclosed herein.

In one embodiment, the long arcs 42, 44 are aligned with the end-planes of the cylindrical (nominal) field-of-view, and data completeness is achieved (from a mathematical point of view using, e.g., Tuy's data completeness condition), thereby enabling improved image quality with reduced cone-beam artifacts. As an example, illustrated schematically in FIG. 9 is a side view of the cylindrical (nominal) field-of-view 80, illustrating relative positioning of a focal spot 82, and the x-ray detector 14. As illustrated, the cylindrical field-of-view 80 is substantially centered, about an isocenter 84 of the C-arm system 10 and the focal spot 82 and the x-ray detector 14 are shown in a position that the gantry assumes, e.g., at the center of a long arc (i.e., for the pivot axis in the home position, and for a fixed position of the C-axis). As illustrated, the focal spot position is in the plane described by the end plane of the cylindrical field of view 80. When the C-gantry is at the position corresponding to the center of the other long arc, the focal spot may assume a position (not shown) in the plane described by the other end plane of the cylindrical field of view. In an embodiment, this may be achieved through a separation of the long arcs 42, 44 by a distance of about 18 cm for a 30 cm detector, and by a distance of about 23 cm for a 40 cm detector. This spacing corresponds to the short arcs 46, 48 spanning approximately 15 and 19 degrees, respectively. In one embodiment the C-axis may be in a fixed position of 7.5 (or 9.5) degrees from a home position for a substantial part of one long arc, and in a fixed position of negative 7.5 (or negative 9.5) degrees from the home position for a substantial part of the other long arc. The example described above is for a specific gantry geometry and assuming full detector readout. Detector readout rate can sometimes be the limiting factor in 3D image quality. A means of increasing the x-ray detector 14 readout rate is to restrict the readout to a portion of the x-ray detector 14 (e.g., at the center of the detector) with the obvious consequence of reducing the field-of-view and, correspondingly, reducing the length of the short arcs 46, 48.

In other embodiments, the short arcs 46, 48 spans may be greater or lesser, resulting in a rectangle that may be wider, or narrower. In one embodiment, each of the short arcs 46, 48 span may be in a range of more than 19 degrees, or less than 15 degrees. The long arcs 42, 44 may span less than 200 degrees, or more than 220 degrees.

Figure 10:
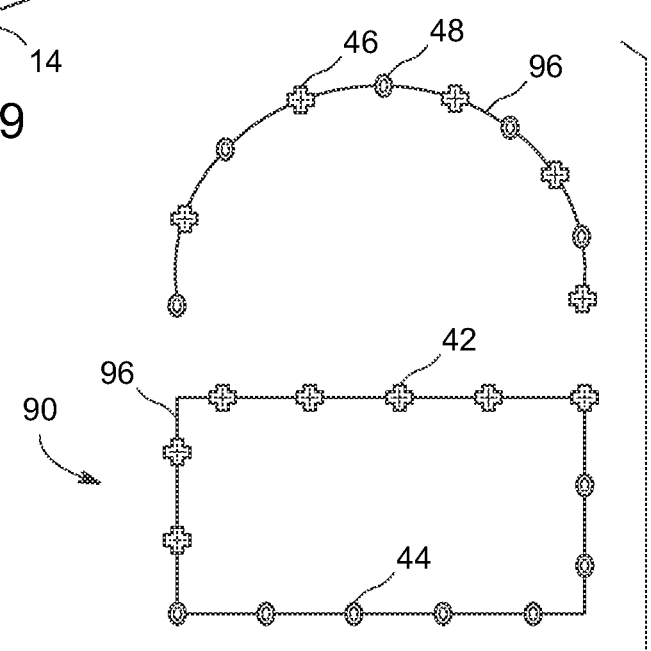
FIG. 10 illustrates a side view and a top plan view of trajectories where the forward long arc and the backward long arc are sampled at interleaved positions according to one or more embodiments disclosed herein.

Referring now to FIG. 10, in an embodiment, the acquisition positions (times) on the forward first long arc 42, the backward second long arc 44, the forward short arc 46 and the backward short arc 48 may be interleaved. As indicated in FIG. 10, distribution of interleaved samples along a rectangular trajectory 96, are illustrated, wherein the "+" denotes a forward spin 42 and short arc 46, and "•" denotes a backward spin 44 and short arc 48. Also shown in an uppermost portion of FIG. 10, is a side view of such an interleaved trajectory (sample points corresponding to the short arcs not shown), wherein the "+" denotes the forward long arc 42, and the "•" denotes a backward long arc 44. This illustrates that the total set of view angles (in the x/y plane, the axial plane) as illustrated at 90, is finer sampled (e.g., 2× finer) than the acquisition angles along a single long arc (corresponding to a standard spin), as known in the art.

In an embodiment the x-ray view acquisition times/positions along the trajectory 40, 50, 60 are chosen such that they have an approximately constant angular spacing (i.e., at times when the angular gantry speed is lower, the sampling rate is also lower). For example, the pivot axis may be driven at a higher speed than the C-axis. Consequently, the X-ray views are acquired at a lower rate while the short arcs of the trajectory (corresponding to a C-axis motion) are traversed, and the X-ray views are acquired at a higher rate while the long arcs of the trajectory (corresponding to a pivot axis motion) are traversed. Angular spacing between projections may be determined as a function of angular position of the individual axes, or, more generally, as the angle between the orientation of the central X-ray (connecting the focal spot and the center of the detector) in 3 dimensions, or similar methods.

In an embodiment, the trajectory 40, 50, 60 is optimized such as to minimize system/gantry vibration during the "turn-around times", e.g., when transitioning from the forward first long arc 42 to the backward second long arc 44. In an embodiment, the overall trajectory 40, 50, 60 within the circumscribing rectangle is optimized such as to minimize gantry vibration (or, conversely, maximize trajectory stability in terms of repeatability etc.). Such an optimization of the trajectory may be achieved based on engineering judgment, simulations of mechanical behavior of the gantry when traversing considered trajectories, or other analyses, or by experimental evaluation. In one embodiment, the trajectory 40, 50, 60 is chosen (within a circumscribing rectangle) such that the instantaneous gantry speed is maximal (given mechanical constraints by gantry and/or drives) for the different axes; in this way the "amount of 3D information collected per unit time" is maximized.

Figure 11:
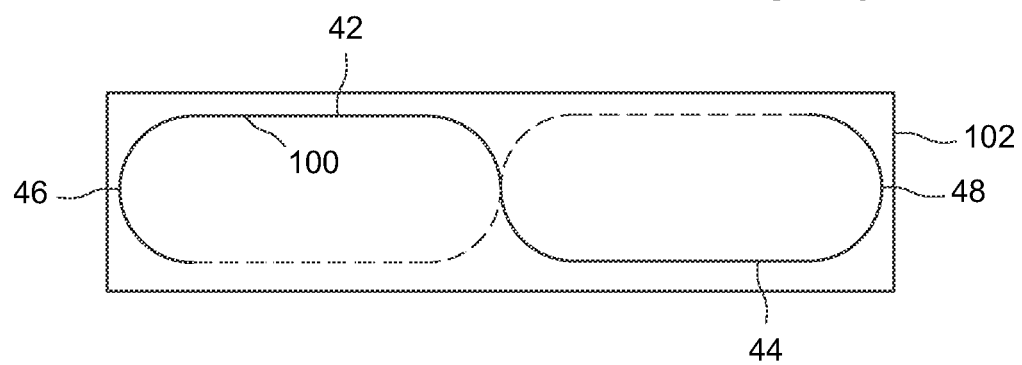
FIG. 11 is a top plan view of a single-pass trajectory according to one or more embodiments disclosed herein.

Referring now to FIG. 11, in an embodiment, a trajectory 100 consists of an open "single-pass" trajectory inscribed within a bounding rectangle 102, similar to bounding rectangle 41 previously described with regard to FIGS. 3-8. In an embodiment this single-pass trajectory 100 is S-shaped, with the start/end-section of the trajectory 100, and more particularly the short arcs 46, 48 being approximately aligned with the short sides of the circumscribing rectangle 102, and the long arcs 42, 44 being aligned with segments of the long sides of the circumscribing rectangle 102, and the start/end-points of the trajectory 100 being approximately at the corners of the circumscribing rectangle 102. In another embodiment the trajectory 100 is a generalized "figure-eight", bounded by the rectangle 102. In yet another embodiment, a central part of the generalized figure-eight trajectory being aligned with a centered spin trajectory, and the "turn-around" sections of the trajectory are smooth curves.

Figure 12:
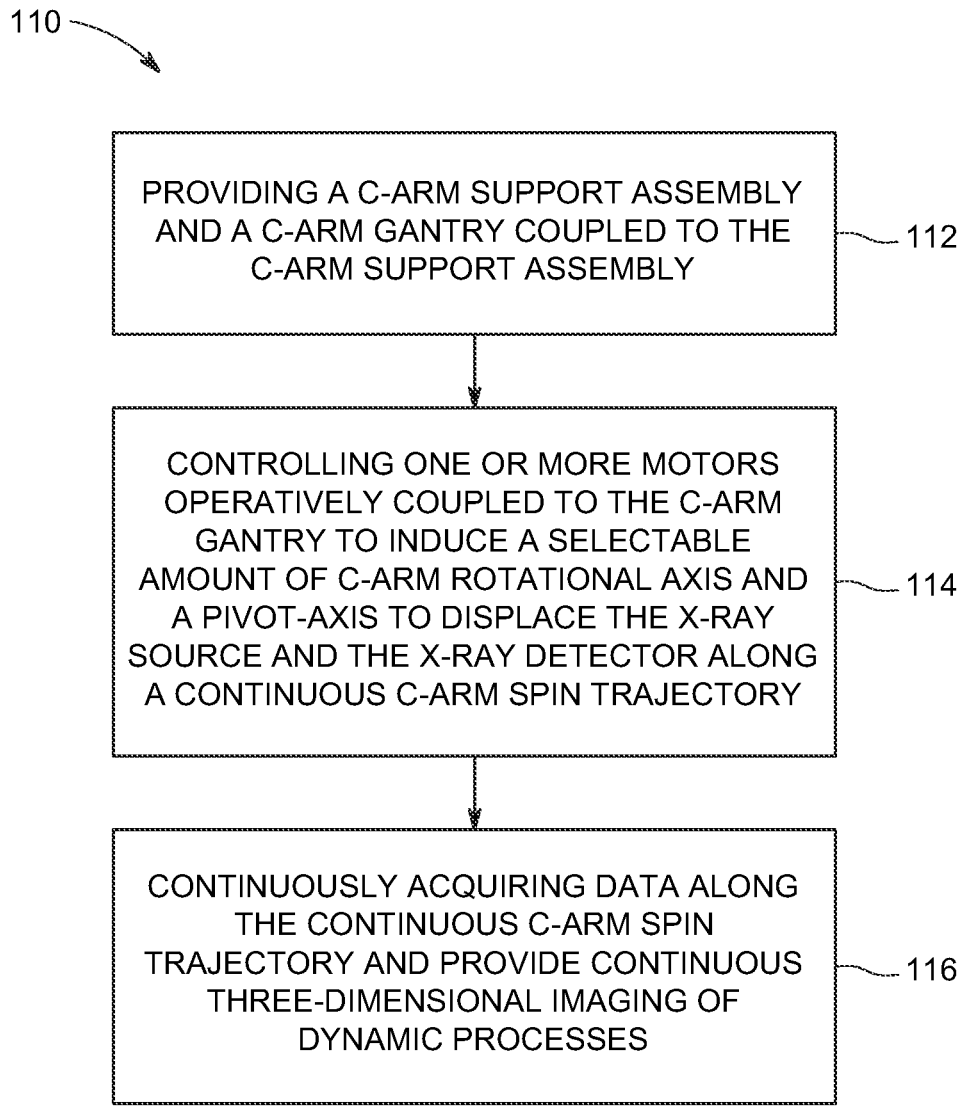
FIG. 12 illustrates a flow chart showing a method for using a C-arm system and continuous C-arm spin acquisition trajectories for dynamic imaging and improved image quality, according to one or more embodiments shown or described herein.

FIG. 12 illustrates a flow chart representative of a method 110 for using a C-arm system, such as system 10 or 30 previously described, and a continuous C-arm spin acquisition trajectory, such as trajectories 40, 50, 60, 100 previously described, for dynamic imaging and improved image quality. In a first step 112, a C-arm support assembly and a C-arm gantry, coupled to the C-arm support assembly, are provided. The C-arm gantry is adapted to retain an x-ray source and an x-ray detector. In a next step 114, the method includes controlling one or more motors operatively coupled to the C-arm gantry to induce a selectable amount of C-arm gantry rotation relative to an object sought to be imaged (anatomy of the patient). The C-arm gantry rotation is about both a C-arm axis and a pivot-axis to displace the x-ray source and the x-ray detector along a continuous C-arm spin trajectory. During the method, data is continuously acquired, in a step 116, along the continuous C-arm spin trajectory to provide continuous three-dimensional imaging of dynamic processes. In one embodiment, the x-ray view acquisition rate is adjusted to the gantry speed, and/or the timing of the x-ray exposures is synchronized with the gantry position, such that x-ray images are acquired for specific pre-determined gantry positions along the continuous C-arm spin trajectory. In one embodiment, continuous three-dimensional imaging of dynamic processes is provided by reconstructing x-ray data acquired during a single pass through the continuous trajectory into a 3D volumetric representation of the imaged volume at the corresponding time instant. In another embodiment, this reconstruction step is performed for a number of time-instants. In one embodiment, some x-ray data may be used for multiple reconstructions, for example when providing reconstructions for time-instants that are separated by less than the amount of time it takes for the gantry to traverse the trajectory once. In yet another embodiment, data corresponding to less than, or more than a single pass through the trajectory may be used for each reconstruction. In one such embodiment, for each reconstruction of a 3D volume, x-ray data acquired during a single long arc and none, one, or both adjoining short arcs is used for the reconstruction. Other methods to provide dynamic 3D information based on the acquired x-ray data may be used as well.

Advantageously, the C-arm system 10, 30 and method 110 disclosed herein provides improved ability to image dynamic processes, improved image quality, and is easy to implement on an existing C-arm system (installed base).

It is to be understood that not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, those skilled in the art will appreciate that certain substitutions, alterations and omissions may be made to the embodiments without departing from the spirit of the invention. It should be readily understood that the specification is not limited to such disclosed embodiments and the appended claims are intended to cover such modifications and arrangements. Accordingly, the foregoing description is meant to be exemplary only, and should not limit the scope of the disclosure as set forth in the following claims. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

What is claimed is:

1. A C-arm system comprising:
   a C-arm support assembly;
   a C-arm gantry coupled to the C-arm support assembly; and
   an x-ray source and an x-ray detector retained by the C-arm gantry, the x-ray source and the x-ray detector fixedly positioned relative to the C-arm gantry and one another during a continuous C-arm spin trajectory comprised of a plurality of short arcs and a plurality of long arcs,
   the C-arm gantry selectively rotatable relative to the C-arm support assembly about both a C-axis and a pivot-axis to continuously and repeatedly displace the x-ray source and the x-ray detector along a continuous C-arm spin trajectory,
   the C-arm system acquiring continuous x-ray data along the continuous C-arm spin trajectory to provide continuous three-dimensional imaging of dynamic processes.

2. The C-arm system of claim 1, wherein the continuous C-arm spin trajectory is a smooth approximation of a substantially rectangular trajectory.

3. The C-arm system of claim 1, wherein the continuous C-arm spin trajectory is a smooth approximation of a substantially elliptical trajectory.

4. The C-arm system of claim 1, wherein a motion along each of a plurality of long arcs of the continuous C-arm spin trajectory utilizes only the pivot-axis along a substantial portion of the long arcs, with the C-axis in a fixed position.

5. The C-arm system of claim 4, wherein a motion along a substantial part of each of a plurality of short arcs of the continuous C-arm spin trajectory utilizes only the C-axis with the pivot-axis in a fixed position.

6. The C-arm system of claim 4, wherein the continuous C-arm spin trajectory is optimized to minimize C-arm gantry vibration when transitioning between each of the plurality of long arcs.

7. The C-arm system of claim 4, wherein the plurality of shorts arcs and the plurality of long arcs include a forward spin action and a backward spin action.

8. The C-arm system of claim 7, wherein the continuous C-arm spin trajectory provides interleaved sampling on the forward spin and the backward spin.

9. The C-arm system of claim 1, wherein a sampling/x-ray data acquisition rate is adjusted to an instantaneous angular speed of the gantry.

10. A C-arm system comprising:
    a C-arm support assembly;
    a C-arm gantry coupled to the C-arm support assembly; and
    an x-ray source and an x-ray detector retained by the C-arm gantry, the x-ray source and the x-ray detector fixedly positioned relative to the C-arm gantry and one another during a continuous C-arm spin trajectory comprised of a plurality of short arcs and a plurality of long arcs, the C-arm gantry selectively rotatable relative to the C-arm support assembly about both a C-arm axis and a pivot-axis to continuously and repeatedly displace the x-ray source and the x-ray detector along a continuous C-arm spin trajectory, wherein a motion along each of a plurality of long arcs of the continuous C-arm spin trajectory utilizes only the pivot-axis, with the C-arm axis in a fixed position, the C-arm system acquiring continuous x-ray data along the continuous C-arm spin trajectory to provide continuous three-dimensional imaging of dynamic processes.

11. The C-arm system of claim 10, wherein the continuous C-arm spin trajectory is a smooth approximation of a substantially rectangular trajectory.

12. The C-arm system of claim 10, wherein the continuous C-arm spin trajectory is a smooth approximation of a substantially elliptical trajectory.

13. The C-arm system of claim 10, wherein the continuous C-arm spin trajectory is optimized to minimize C-arm gantry vibration when transitioning between each of the plurality of long arcs.

14. The C-arm system of claim 10, wherein the plurality of shorts arcs and the plurality of long arcs include a forward spin action and a backward spin action.

15. The C-arm system of claim 10, wherein the continuous C-arm spin trajectory provides interleaved sampling on the forward spin and the backward spin.

16. The C-arm system of claim 10, wherein a sampling/x-ray data acquisition rate is adjusted to an instantaneous angular speed of the gantry.

17. A method for using a C-arm system comprising:
providing a C-arm support assembly and a C-arm gantry coupled to the C-arm support assembly;
providing an x-ray source and an x-ray detector retained by the C-arm gantry, the x-ray source and the x-ray detector fixedly positioned relative to the C-arm gantry and one another during a continuous C-arm spin trajectory comprised of a plurality of short arcs and a plurality of long arcs;
controlling one or more motors operatively connected to the C-arm gantry to induce a selectable amount of C-arm gantry rotation relative to an imaged object along the continuous C-arm spin trajectory; and
continuously acquiring x-ray data along the continuous C-arm spin trajectory to provide continuous three-dimensional imaging of dynamic processes.

18. The method of claim 17, wherein the continuous C-arm spin trajectory comprises a plurality of short arcs and a plurality of long arcs.

19. The method of claim 17, wherein the C-arm gantry rotation is about both a C-axis and a pivot-axis to displace the x-ray source and the x-ray detector along the continuous C-arm spin trajectory.

20. The method of claim 17, wherein at least one of an X-ray view acquisition rate is adjusted to a gantry speed or the timing of x-ray exposures is synchronized with a position of the C-arm gantry, such that images are acquired for specific pre-determined gantry positions along the continuous C-arm spin trajectory.

* * * * *